United States Patent [19]

Hasegawa et al.

[11] 4,352,941

[45] Oct. 5, 1982

[54] PROCESS FOR PURIFICATION OF PHENYLHYDRAZINE

[75] Inventors: Shinichi Hasegawa, Hirakata; Yuji Ueda, Izumi; Hiroshige Tomita, Toyonaka, all of Japan

[73] Assignee: Sumitomo Chemical Company, Limited, Osaka, Japan

[21] Appl. No.: 919,992

[22] Filed: Jun. 28, 1978

[30] Foreign Application Priority Data

Jul. 6, 1977 [JP] Japan ................................. 52/81422

[51] Int. Cl.³ ......................................... C07C 109/04
[52] U.S. Cl. ................................................. 564/314
[58] Field of Search ......................... 260/569; 564/314

[56] References Cited

U.S. PATENT DOCUMENTS

| 2,876,173 | 3/1959 | Nicolaisen | 260/569 X |
| 3,203,989 | 8/1965 | Hupfer | 260/569 |
| 3,354,200 | 11/1967 | Huebner | 260/569 X |
| 3,433,788 | 3/1969 | Somekh et al. | 260/582 X |

Primary Examiner—Robert V. Hines
Attorney, Agent, or Firm—Birch, Stewart, Kolasch & Birch

[57] ABSTRACT

Crude phenylhydrazine is distilled in the presence of a glycol to obtain phenylhydrazine of high purity in a high yield.

9 Claims, No Drawings

PROCESS FOR PURIFICATION OF PHENYLHYDRAZINE

The present invention relates to a process for purification of phenylhydrazine. More particularly it relates to a process for producing phenylhydrazine of high quality comprising distilling crude phenylhydrazine in the presence of a glycol.

Production of phenylhydrazine (hereinafter referred to as "PHD") by diazotization of aniline, followed by reduction and hydrolysis is well known. After the hydrolysis with an acid, the resulting acid salt of PHD is usually treated as follows: the salt is separated by filtration and neutralized with an aqueous alkali solution to liberate PHD; the resulting PHD is recovered by separation or extraction with an organic solvent, followed by removal of water or the organic solvent by evaporation; and the recovered PHD is subjected to distillation.

In this process, however, the yield and quality of PHD are not always sufficient. In particular, satisfactory results are not easily obtainable in the dissolution-in-acetic acid test according to JIS (Japanese Industrial Standard) K 8795. Further, the process requires filtration of the resulting PHD salt, which is very troublesome, and the problem of filtrate treatment arises therefrom.

As the result of an extensive study to overcome the said drawbacks present in the known process, it has now been found that the presence of a glycol during the distillation of crude PHD is quite effective in affording PHD of high quality, which satisfies the dissolution-in-acetic acid test, with an excellent yield. It has also been found that the troublesome operation of filtration of the PHD salt can be omitted by neutralizing the reaction mixture containing the PHD salt, obtained as the result of the hydrolysis, with an alkali and subjecting the resulting heterogeneous solution to separation or extraction with a water-immiscible organic solvent to recover a crude PHD solution, which is then distilled in the presence of a glycol.

Accordingly, a basic object of the present invention is to provide an improved process for obtaining PHD of high quality from crude PHD. Another object of this invention is to provide an improved process for production of PHD of high quality from the PHD salt prepared by diazotization of aniline, followed by reduction and hydrolysis. A further object of the invention is to provide an improved process for production of PHD of high quality with an excellent yield from the reaction mixture containing the PHD salt obtained by diazotization of aniline, followed by reduction and hydrolysis, without any troublesome filtration operation. These and other objects of the invention will be apparent to those skilled in the art from the foregoing and subsequent descriptions.

According to the present invention, PHD of high quality is obtained by distillation of crude PHD in the presence of a glycol.

The crude PHD may be obtained by any conventional process. A typical and representative example of the conventional processes for production of PHD comprises diazotization of aniline, followed by reduction and hydrolysis [cf. Organic Syntheses, Coll. Vol. II].

In such a typical and representative process, the recovery of PHD from the reaction mixture in the hydrolysis step has heretofore been effected by cooling the reaction mixture so as to precipitate the PHD salt therein and collecting the precipitated PHD salt by filtration. However, cooling and filtering take a long time and require a troublesome operation. In addition, a part of the PHD salt is kept in the filtrate so that the loss amount is considerable. Since the filtrate has a high organic COD value, its discard produces a separate problem. The recovery of the PHD salt in the filtrate by the use of any appropriate solvent decreases the loss, but various impurities are simultaneously recovered so that the quality of the PHD salt is deteriorated.

According to this invention, the reaction mixture containing the PHD salt in the hydrolysis step is neutralized with an alkali to liberate PHD, and the liberated PHD is separated as a solution or extracted with a water-immiscible organic solvent. In the neutralization, the alkali is usually employed in the form of an aqueous solution having a concentration of 10 to 50% by weight. As the alkali, there may be used an alkali metal hydroxide (e.g. sodium hydroxide, potassium hydroxide) or an alkaline earth metal hydroxide (e.g. magnesium hydroxide, calcium hydroxide). Examples of the water-immiscible organic solvent for extraction of the crude PHD are aromatic hydrocarbons such as benzene, toluene and xylene. The resultant PHD solution is distilled to eliminate the solvent, whereby crude PHD is obtained. Then, the crude PHD is subjected to distillation in the presence of a glycol to obtain pure PHD. Since a filtration step is not employed, the troublesome operation which results therefrom and the loss of the PHD salt into the filtrate can be avoided, and the yield of PHD on the basis of aniline is highly improved and usually reaches about 94 to 95%.

The glycol to be used in the distillation of crude PHD according to this invention is not particularly limited, but preferred are those which are easily available as a commercial product and whose boiling point is properly apart from that of PHD. Specific examples are ethylene glycol, diethylene glycol, trimethylene glycol, propylene glycol, tetramethylene glycol, butylene glycol, etc. The amount of the glycol added to crude PHD is not particularly limited and may be usually from 0.1 to 5% by weight based on the weight of crude PHD.

Distillation of a mixture comprising the crude PHD and the glycol may be carried out by a per se conventional procedure, preferably using a rectification tower having 5 or more theoretical plates under a reduced pressure of not more than 30 mmHg (particularly around 10 mmHg). The distillation temperature depends on the pressure and may be controlled favorably to a temperature of not higher than 150° C., particularly from about 125° to 135° C., in order to prevent the thermal decomposition of PHD. The distillate collected in the early stage is removed in an amount of 1 to 10% by weight based on the weight of the crude PHD. After the removal of the distillate collected in said early stage, simple distillation may be effected in place of the rectification under the pressure and temperature conditions as set forth above.

Prior to the said distillation, the crude PHD is preferably treated with an alkali metal or alkaline earth metal hydroxide while heating so that the coloration of the PHD product obtained from the crude PHD is more effectively reduced. Examples of the alkali metal or alkaline earth metal hydroxide are hydroxides of sodium, potassium, magnesium, calcium, etc. These alkali metal or alkaline earth metal hydroxides may be used alone or in combination in the form of a solid or an aqueous solution. In case of the aqueous solution, the concentration thereof may be usually from about 2 to 50% by weight. The amount of the alkali metal or alkaline earth metal hydroxides is normally from about 2 to 200% by weight on the basis of the weight of the crude PHD. The treatment may be effected at a temperature of about 40° to 150° C., preferably of about 70° to 120° C., for a period of about 5 to 60 minutes.

As understood from the above descriptions, the present invention makes it possible to obtain PHD of high quality in an excellent yield from crude PHD, particularly prepared by diazotization of aniline and subsequent reduction and hydrolysis, without troublesome operations, and therefore the invention is highly advantageous from the industrial viewpoint.

Practical and presently preferred embodiments of the present invention are illustratively shown in the following examples wherein parts are by weight.

EXAMPLE 1

Aniline was diazotized with sodium nitrite, reduced with a mixed solution containing sodium sulfite and sodium bisulfite and hydrolyzed with hydrochloric acid. The resulting PHD hydrochloride was cooled and separated as a wet cake by filtration. The wet cake was neutralized with an aqueous sodium hydroxide solution to liberate PHD, and the PHD was recovered from the aqueous solution by extraction with toluene. Thereafter, the solvent was removed by evaporation to obtain crude PHD.

When the crude PHD was purified by the usual distillation, the quality of the purified product was only of such a degree that the dissolution-in-acetic acid test according to JIS K 8795 showed a turbidity grade of "slightly turbid to turbid".

The crude PHD (500 parts) and 10 parts of ethylene glycol were charged in a distilling flask equipped with a packed tower having 6 theoretical plates and rectified under reduced pressure at a reflux ratio of 15 to obtain 16 parts of a top fraction. Thereafter, the residual liquor in the flask was subjected to simple distillation under reduced pressure to obtain 487 parts of purified PHD. This PHD showed a turbidity grade of "clear" in the dissolution-in-acetic acid test according to JIS K 8795.

COMPARATIVE EXAMPLE 1

The crude PHD (500 parts) having a poor dissolution-in-acetic acid as used in Example 1 was charged in a distilling flask equipped with a packed tower having 6 theoretical plates and rectified under reduced pressure at a reflux ratio of 15 to separate 10 parts of a top fraction. Thereafter, the residual liquor in the flask was subjected to simple distillation under reduced pressure to obtain 484 parts of purified PHD. The purified PHD showed the same turbidity grade of "slightly turbid" as before the above treatment, as examined for the turbidity of its acetic acid solution.

EXAMPLE 2

Using the crude PHD having a poor dissolution-in-acetic acid as used in Example 1 and varying the kinds and amounts of glycols, the same procedures as in Example 1 were carried out. The results obtained are shown in Table 1.

TABLE 1

| Glycol | Amount of crude PHD charged (part) | Amount of glycol charged (part) | Amount of top fraction (part) | Yield of purified PHD (part) | Turbidity of acetic acid solution |
|---|---|---|---|---|---|
| Ethylene glycol | 500 | 30 | 41 | 480 | Clear |
| Ethylene glycol | 500 | 15 | 20 | 483 | Clear |
| Ethylene glycol | 500 | 5 | 12 | 482 | Almost clear |
| 1,2-Propylene glycol | 500 | 10 | 18 | 481 | Clear |
| 1,3-Propylene glycol | 500 | 10 | 17 | 483 | Clear |
| Diethylene glycol | 500 | 10 | 19 | 479 | Almost clear |
| 1,2-Butylene glycol | 500 | 10 | 18 | 481 | Almost clear |
| 2,3-Butylene glycol | 500 | 10 | 20 | 477 | Clear |

EXAMPLE 3

In a 1 liter flask equipped with a stirrer, a dropping bottle, a thermometer and a condenser, 456 parts of 20% hydrochloric acid and 93 parts of aniline were charged. Diazotization was carried out with addition of 201 parts of 36% aqueous sodium nitrite solution from the dropping bottle, during which the content of the flask was cooled to 0° C. or less with a freezing mixture. Thus, 750 parts of a reaction solution was obtained. The solution was then poured, at 30° C. or less, into a separately prepared mixed solution comprising 189 parts of sodium sulfite, 104 parts of sodium bisulfite and 672 parts of water. The mixture was kept at 30° C. for 1 hour, elevated to 85° C. and kept at the same temperature for 1 hour, during which reduction was carried out.

The reduction solution was elevated to 95° C., and 208 parts of 35% hydrochloric acid was added from a dropping bottle. The solution was kept at the same temperature for 2 hours, during which hydrolysis was carried out. Thereafter, the reaction mixture was cooled to room temperature, neutralized by adding 356 parts of 45% sodium hydroxide from a dropping bottle and extracted twice with 400 parts of toluene. Thus, the liberated PHD was recovered from the neutralized solution.

The separated toluene layers were combined and freed from toluene by evaporation under reduced pressure. Thus, 107 parts of crude PHD was obtained as the residue.

This crude PHD was mixed with 2.2 parts of ethylene glycol and subjected to rectification and simple distillation to obtain 102 parts of purified PHD. The purified PHD showed a turbidity grade of "clear", as examined for the turbidity of its acetic acid solution.

COMPARATIVE EXAMPLE 2

In the same manner as in Example 3, reactions (i.e. diazotization, reduction, hydrolysis and neutralization), extraction, removal of the extracting solvent and separation were carried out to obtain 108 parts of crude PHD. Thereafter, the crude PHD was subjected to rectification and simple distillation to obtain 101 parts of purified PHD. The purified PHD showed a turbidity grade of "turbid", as examined for the turbidity of its acetic acid solution.

EXAMPLE 4

In the same manner as in Example 3, reactions (i.e. diazotization, reduction, hydrolysis and neutralization), extraction, removal of the extracting solvent and separation were carried out to obtain 110 parts of crude PHD. This crude PHD was mixed with 33 parts of 10% aqueous sodium hydroxide solution, heated to 90° C., kept at 90° C. with stirring for 1 hour, cooled to room temperature and transferred to a separating funnel. Thus, 128 parts of PHD was obtained as an upper layer. Thereafter, this PHD layer was mixed with 2.2 parts of ethylene glycol and subjected to rectification and simple distillation to obtain 102 parts of purified PHD. The purified PHD showed a turbidity grade of "clear", as examined for the turbidity of its acetic acid solution, and it was almost colorless and displayed a Gardner Scale No. 1.

What is claimed is:

1. A process for producing phenylhydrazine of high clarity, which comprises distilling crude phenylhydrazine in the presence of a glycol selected from the group consisting of ethylene glycol, diethylene glycol, trimethylene glycol, propylene glycol, tetramethylene glycol and butylene glycol.

2. The process according to claim 1, wherein the glycol is present in an amount of 0.1 to 5% by weight based on the weight of the crude phenylhydrazine.

3. The process according to claim 1, wherein the distillation is effected using a rectification tower having not less than 5 theoretical plates.

4. The process according to claim 1, wherein the distillation is effected at a temperature of not higher than 150° C. under a pressure of not higher than 30 mmHg.

5. The process according to claim 1, wherein the crude phenylhydrazine is obtained by diazotization of aniline, followed by reduction and hydrolysis to give a reaction mixture containing an acid salt of phenylhydrazine, subjecting the reaction mixture to neutralization with an alkali to liberate phenylhydrazine and then recovering the liberated crude phenylhydrazine by separation or extraction with a water-immiscible organic solvent.

6. The process according to claim 1, wherein the crude phenylhydrazine is treated with at least one hydroxide of an alkali metal or an alkaline earth metal while heating prior to the distillation.

7. The process according to claim 6, wherein the hydroxide is sodium hydroxide, potassium hydroxide, magnesium hydroxide or calcium hydroxide.

8. The process according to claim 6, wherein the hydroxide is used in an amount of 2 to 200% by weight based on the weight of the crude phenylhydrazine.

9. The process according to claim 6, wherein the treatment is effected at a temperature of 40° to 150° C.

* * * * *